(12) United States Patent
Ooura et al.

(10) Patent No.: US 8,834,377 B2
(45) Date of Patent: Sep. 16, 2014

(54) ULTRASONIC PROBE

(75) Inventors: Kouji Ooura, Kanagawa (JP); Hirokazu Fukase, Kanagawa (JP)

(73) Assignee: Konica Minolta, Inc., Tokyo (JP)

( * ) Notice: Subject to any disclaimer, the term of this patent is extended or adjusted under 35 U.S.C. 154(b) by 978 days.

(21) Appl. No.: 12/679,390

(22) PCT Filed: Oct. 14, 2008

(86) PCT No.: PCT/JP2008/002905
§ 371 (c)(1),
(2), (4) Date: Mar. 22, 2010

(87) PCT Pub. No.: WO2009/050881
PCT Pub. Date: Apr. 23, 2009

(65) Prior Publication Data
US 2010/0198077 A1 Aug. 5, 2010

(30) Foreign Application Priority Data
Oct. 15, 2007 (JP) ................. 2007-267610

(51) Int. Cl.
*A61B 8/14* (2006.01)
*A61B 8/00* (2006.01)
*B06B 1/06* (2006.01)
*A61B 8/08* (2006.01)

(52) U.S. Cl.
CPC . *A61B 8/08* (2013.01); *A61B 8/463* (2013.01); *B06B 1/0622* (2013.01); *A61B 8/488* (2013.01)
USPC .......................................................... 600/459

(58) Field of Classification Search
USPC .............. 601/2; 600/407, 411, 427, 371, 462, 600/463, 467, 459; 310/334, 366, 322, 335
See application file for complete search history.

(56) References Cited

U.S. PATENT DOCUMENTS 4,701,659 A   10/1987   Fujii et al.
6,426,582 B1 *  7/2002   Niederer et al. .............. 310/309
(Continued)

FOREIGN PATENT DOCUMENTS

JP   61-78300 A   4/1986
JP   61-103399 A   5/1986
(Continued)

OTHER PUBLICATIONS

International Search Report for PCT/JP2008/002905.
(Continued)

*Primary Examiner* — Elmer Chao
(74) *Attorney, Agent, or Firm* — Holtz, Holtz, Goodman & Chick PC (57) ABSTRACT

An ultrasonic probe that enables the sensibility irregularity between arrays to be reduced is disclosed. This piezoelectric element contains: a piezoelectric element 1; a first electrode layer 2 formed on one side of the piezoelectric element 1; one or more conductive acoustic matching layers 5 layered via an adhesive layer 4 on the first electrode layer 2; a first film 7 which is layered via an adhesive layer 6 on the acoustic matching layer 5 and in which an electrode pattern is formed on the side of the adhesive layer 6; a second electrode layer 3 formed on the other side of the piezoelectric element 1; and a second film 15 which is layered via an adhesive layer 14 on the second electrode layer 3 and in which an electrode pattern is formed on the side of the adhesive layer 14, wherein the adhesive layers 4, 6 and 14 are thermosetting two-component type adhesives in which graphite powder is uniformly distributed therein.

6 Claims, 8 Drawing Sheets

(56) References Cited

U.S. PATENT DOCUMENTS

| | | | |
|---|---|---|---|
| 6,809,268 B2* | 10/2004 | Hayashi et al. | 174/260 |
| 2001/0055435 A1* | 12/2001 | Biagi et al. | 385/7 |
| 2003/0040818 A1* | 2/2003 | Pletner et al. | 700/60 |
| 2003/0176124 A1* | 9/2003 | Koike et al. | 442/16 |
| 2003/0189391 A1 | 10/2003 | Shimizu | |
| 2005/0099097 A1* | 5/2005 | Baumgartner et al. | 310/334 |
| 2005/0272183 A1* | 12/2005 | Lukacs et al. | 438/109 |

FOREIGN PATENT DOCUMENTS

| | | |
|---|---|---|
| JP | 04-048900 A | 2/1992 |
| JP | 05-023341 A | 2/1993 |
| JP | 06-000184 A | 1/1994 |
| JP | 06-014396 A | 1/1994 |
| JP | 07-123497 A | 5/1995 |
| JP | 08-122310 A | 5/1996 |
| JP | 2000-253496 A | 9/2000 |
| JP | 2001-258097 A | 9/2001 |
| JP | 2003-299196 A | 10/2003 |
| JP | 2005-308691 A | 11/2005 |
| JP | 2005-323630 A | 11/2005 |

OTHER PUBLICATIONS

Japanese Office Action for Application No. 2009-537915 dated Jul. 10, 2013.

* cited by examiner

— ULTRASONIC PROBE IN THE FOURTH EMBODIMENT OF THE PRESENT INVENTION

— CONVENTIONAL ULTRASONIC PROBE

FIG. 7B

— ULTRASONIC PROBE IN THE FOURTH EMBODIMENT OF THE PRESENT INVENTION

— CONVENTIONAL ULTRASONIC PROBE

Figure 8:
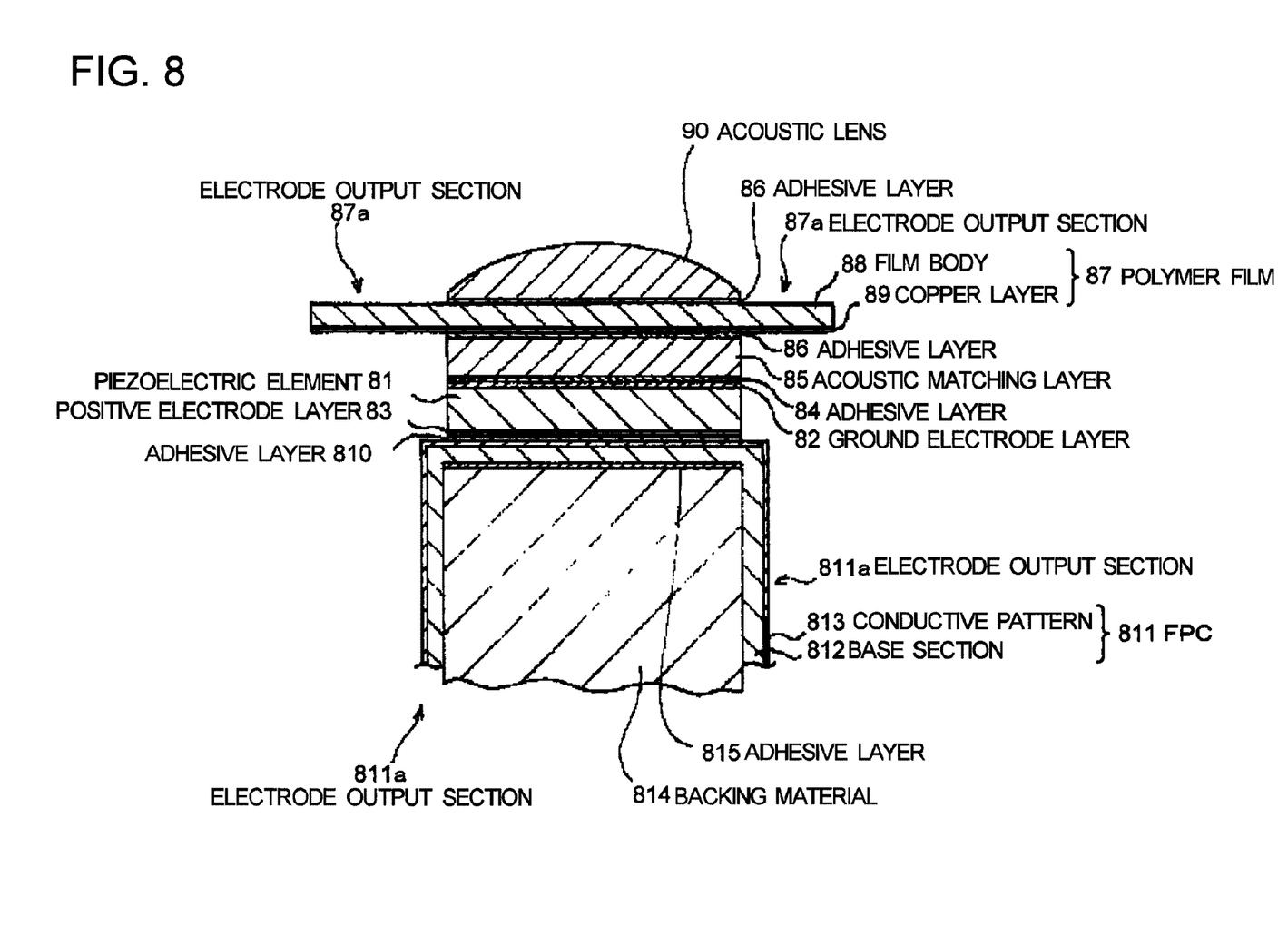
FIG. 8 is a schematic sectional view of a conventional ultrasonic probe.

FIG. 8 ically connected, respectively, because insulating epoxy resins are pressed, heated and cured and consequently adhered in very thin manners. Irrespectively of the existence of the thin insulating layer, a tunnel effect, a Schottky conduction, an impurity conduction, or the like causes the charges from being shifted. When the insulating layer is uniformly thin, the conduction resistance is constant. However, the thicknesses of the insulating adhesive layers 84, 86 and 810 are not constant. Thus, with the surface roughness of the opposite conductor member, a conduction resistance exists under a certain probability.

ULTRASONIC PROBE

TECHNICAL FIELD

The present invention relates to an ultrasonic probe that is connected to an ultrasonic diagnostic apparatus, which can emit ultrasonic waves into the body of an examinee and display the picture of the inside of the body interior, from the ultrasonic waves reflected by a boundary between respective body elements.

BACKGROUND ART

The prior art of the present invention will be described below by using the drawings. FIG. 8 is a view showing the configuration of a conventional ultrasonic probe (for example, see the following patent document 1). In the explanation of this drawing, [UP] and [DOWN] are assumed to indicate the upward direction and the downward direction in the plane of the drawing paper, respectively. In FIG. 8, a piezoelectric element 81 having electrodes on both surfaces is an element for transmitting and receiving ultrasonic waves. On the upper surface of the piezoelectric element 81, a ground electrode layer 82 is formed as a first electrode layer, and on the lower surface, a positive electrode layer 83 is formed as a second electrode layer, respectively, in advance.

A conductive acoustic matching layer 85 is intended to efficiently transmit and receive the ultrasonic waves to a test subject (living body) and layered on the upper surface (the side of the ground electrode layer 82) of the piezoelectric element 81, via a compressively-cured insulating adhesive layer 84. On the acoustic matching layer 85, a polymer film 87 made of polyimide and the like is layered via the compressively-cured insulating adhesive layer 84. The polymer film 87 is composed of the two layers of a film body 88 as an acoustic matching layer and a conductor layer (copper layer) 89 formed on the side of an adhesive layer 86 of this film body 88. Although not shown in FIG. 8, in order to further attain the acoustic matching with the living body, there is a case that a second acoustic matching layer made of a polymer material and the like is layered via an adhesive layer, on the surface of the film body 88. Moreover, an acoustic lens 90 is placed on the surface of the second acoustic matching layer.

By the way, the plurality of acoustic matching layers, which are layered on the piezoelectric element 81 and the piezoelectric element 81, are divided into a plurality of arrays, which are electrically independent of each other, by dicing. On the lower surface (the side of the positive electrode layer 83) of the piezoelectric element 81, an FPC 811 is layered via a compressively-cured insulating adhesive layer 810. In this FPC 811, a base unit 812 made of polyimide is formed, and a conductive pattern 813 corresponding to the piezoelectric element 81 is formed on the side of the piezoelectric element 81 on this base unit 812. Also, both sides of the FPC 811 protrude from the layered portion of the piezoelectric element 81, and electrode extracting units 811a are formed on both ends of the protrusions. A backing material 814 is attached via an adhesive layer 815 to the side of the base unit 812 of the FPC 811 and mechanically supports the piezoelectric element 81 and acoustically brakes the piezoelectric element 81 and consequently makes an ultrasonic pulse waveform short.

In the conventional ultrasonic probe, the ground electrode layer 82 in the piezoelectric element 81 and the conductive acoustic matching layer 85, and the acoustic matching layer 85 and the polymer film 87 on which the conductive pattern is formed, and the positive electrode layer 83 in the piezoelectric element 81 and the conductive pattern 813 in the FPC 811 are electrically connected, respectively, because insulating epoxy resins are pressed, heated and cured and consequently adhered in very thin manners. Irrespectively of the existence of the thin insulating layer, a tunnel effect, a Schottky conduction, an impurity conduction, or the like causes the charges from being shifted. When the insulating layer is uniformly thin, the conduction resistance is constant. However, the thicknesses of the insulating adhesive layers 84, 86 and 810 are not constant. Thus, with the surface roughness of the opposite conductor member, a conduction resistance exists under a certain probability.

Depending on a place, the thickness is very close to 0. In short, there are the portions where the ground electrode layer 82 in the piezoelectric element 81 and the acoustic matching layer 85, and the acoustic matching layer 85 and the conductive layer 89 in the polymer film 87, and further the positive electrode layer 83 in the piezoelectric element 81 and the conductive pattern 813 in the FPC 811 are in contact, respectively. Thus, the conduction resistances of those contact portions are small. Hence, depending on the adhesion state between the materials, namely, the total area of the contact portions between the mutual materials, the conduction resistance is changed.

The piezoelectric element 81, the conductive acoustic matching layer 85, the polymer film 87 where the conductive pattern is formed, and the conductive pattern of the FPC 811, which are adhesively layered via the insulating epoxy resins, are divided into the plurality of arrays, which are electrically independent of each other, by dicing. However, the conduction resistances of the electrode connectors are irregular in the respective arrays. As a result, there was a problem that the sensitivities were irregular between the arrays. A higher frequency orientation makes its problem severer, in recent years in which the width of the division electrode is narrower.

Also, as a method of solving the foregoing problems, there is a method of using a conductive paste, or an anisotropic conductive adhesive that has a conductivity only in a thickness direction, instead of the adhesive of the insulating epoxy resin.

Patent Document 1: Japanese Patent No. 3423788 (Pages 1 and 2, FIG. 2)

However, in the conductive paste that exhibits the conductivity because a conductive path is generated by the volume contraction caused by the thermal curing or by the low temperature sintering between metal powder, or in the anisotropic conductive adhesive in which micro conductive particles are uniformly distributed in a one-component type adhesive that is high in insulation, its curing temperature is high such as 100 deg C. or more. When the polarization-treated piezoelectric element is placed under the high temperature environment such as 100 deg C. or more, the piezoelectric property is lost, which causes the practical use of the conductive paste or anisotropic conductive adhesive from being prevented. Also, the conductive paste and the anisotropic conductive adhesive have the problem that they are expensive.

DISCLOSURE OF THE INVENTION

The present invention is proposed in order to solve the above-mentioned conventional problems and intended to provide an ultrasonic probe of a structure in which a quality is kept good, and the sensibility irregularity between arrays is small, and the working property is good.

The ultrasonic probe according to the present invention comprises:
  a piezoelectric element;
  a first electrode layer formed on one side of said piezoelectric element;

one or more conductive acoustic matching layers layered via an adhesive layer on said first electrode layer;

a first film which is layered via an adhesive layer on said acoustic matching layer, an electrode pattern being formed on said adhesive layer side thereof;

a second electrode layer formed on the other side of said piezoelectric element; and a second film which is layered via an adhesive layer on said second electrode layer, an electrode pattern being formed on said adhesive layer side thereof, wherein in at least one or more of said adhesive layers, graphite powder is uniformly distributed in said adhesive.

Also, a configuration in which a backing material is contained on the other side of the second film and also the adhesive layer is a thermosetting two-component type adhesive is a preferable aspect of the present invention.

With this configuration, electrical gaps between surfaces of respective layers are filled with the graphite powder so that the electrical connection can be reinforced, and the irregularities of the conduction resistances of the piezoelectric element, the conductive acoustic matching layer, the polymer film on which the conductive pattern is formed, and the electrical connector in the conductive pattern of the FPC, which are adhesively layered, are small which can reduce the sensibility irregularity between the arrays.

Also, the ultrasonic probe according to the present invention has a configuration in which a 10-point average roughness (Rz) on the surfaces of the electrode layers formed on both surfaces of the piezoelectric element is in a range from 3.5 μm to 6.5 μm and an average particle diameter of the graphite powder is in a range from 3.5 μm to 6.5 μm.

With this configuration, the graphite powder intrudes into the concave and convex portions on the surface of the piezoelectric element, and the adhesive property between the mutual materials, namely, the contact area between the mutual materials is increased, thereby decreasing the irregularity of the conduction resistance of the electric connector. As a result, the sensibility irregularity between the arrays is reduced. Also, since the concave depth of the piezoelectric element and the diameter of the graphite powder are equal in size, the mutual materials can be adhered in the very thinly manner. Thus, the absorption, reflection and dispersion losses of the ultrasonic waves, which are caused by the adhesive or the graphite powder inside the adhesive, are suppressed, which results in the improvement of the sensibility of the ultrasonic probe.

Moreover, the ultrasonic probe according to the present invention has a configuration in which the graphite powder is mixed in an adhesive layer 1 which is located between the first electrode layer formed on one side of the piezoelectric element and one or more conductive acoustic matching layers, and an adhesive layer 2 which is located between one or more conductive acoustic matching layers and the first film on which the electrode pattern is formed, and tungsten powder is mixed in an adhesive layer 3 which is located between the second electrode layer formed on the other side of the piezoelectric element and the second film on which the electrode pattern is formed.

With this configuration, the difference of the acoustic impedance between the adhesive layer 1, the adhesive layer 2 and the conductive acoustic matching layer is decreased, and the difference of the acoustic impedance between the adhesive layer 3, the electrode of the second film, and the backing material is decreased. Thus, the reflection loss of the ultrasonic waves that are generated by the boundary surface between acoustic media is suppressed, which results in the improvement of the sensibility of the ultrasonic probe.

Moreover, the ultrasonic probe according to the present invention has a configuration that for the piezoelectric element for generating the ultrasonic waves, a complex piezoelectric body is used in which the piezoelectric element where electrodes are formed on both surfaces is cut into an angular shape, and resin is embedded.

With this configuration, the acoustic impedance of the piezoelectric element is decreased, and the matching property with the living body organization is made better. As a result, the acoustic transmission loss is reduced, and the sensibility of the ultrasonic probe is improved.

The present invention can provide the ultrasonic waves in which, when the piezoelectric element, the conductive acoustic matching layer, the first film on which the electrode pattern is formed, and the second film where the electrode pattern is formed are layered and adhered, the thermosetting two-component type adhesive in which the graphite powder is uniformly distributed is used, thereby reducing the irregularity of the conduction resistance of the electric connector, and as a result, there is the effect of the reduction in the sensibility irregularity between the arrays.

BEST MODE FOR CARRYING OUT THE INVENTION

The ultrasonic probe according to the embodiment of the present invention will be described below by using the drawings.

Figure 1:
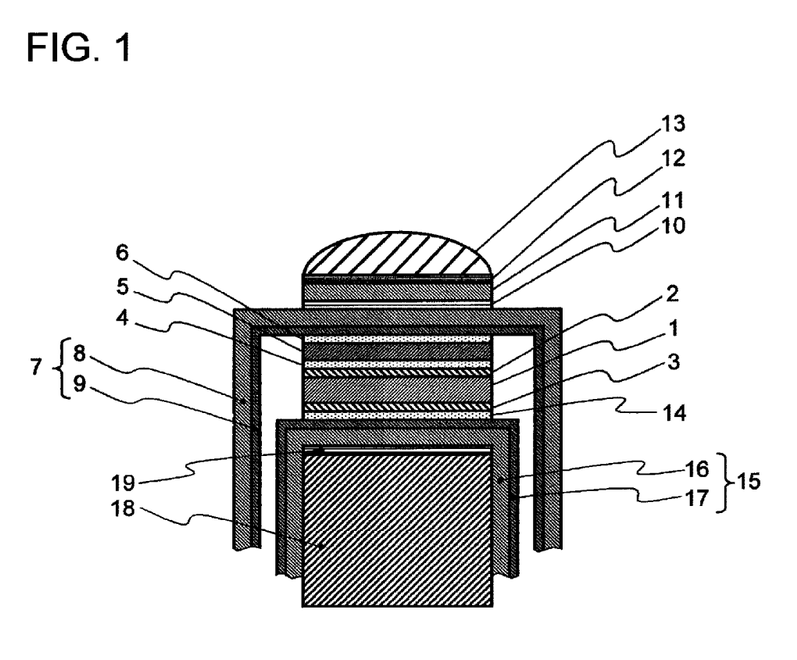
FIG. 1 is a schematic sectional view of an ultrasonic probe in a first embodiment according to the present invention.

FIG. 1 shows the ultrasonic probe in the first embodiment according to the present invention. FIG. 1 is the sectional view in the short axis direction of the ultrasonic probe. By the way, in the explanation of this drawing, [UP] and [DOWN] are assumed to indicate the upward direction and the downward direction in the plane of the drawing paper, respectively (similarly also in FIGS. 4 and 6). In FIG. 1, a piezoelectric element 1 is a piezoelectric element in which a piezoelectric ceramics such as a PZT group and the like, a single crystal, and a polymer such as PVDF and the like are used. On one surface of each of a plurality of piezoelectric elements 1, a ground electrode layer 2 is formed as a first electrode layer, and on the other side, a positive electrode layer 3 is formed as a second electrode layer, respectively, in advance.

In this embodiment, the ground electrode layer 2 and the positive electrode layer 3 are assumed to be the gold sputter electrode layers whose thicknesses effective for the attainment of a high frequency are about 1000 angstrom. However, their materials are not limited. On the side of the ground electrode layer 2 in the piezoelectric element 1, a conductive acoustic matching layer 5 for efficiently transmitting ultrasonic waves is layered via a thermosetting two-component type adhesive layer 4 in which graphite powder is uniformly distributed therein. For the conductive acoustic matching layer 5, for example, graphite and the like are used. Moreover, on the acoustic matching layer 5, a polymer film 7 as a first film is layered via a thermosetting two-component type adhesive layer 6 in which the graphite powder is uniformly distributed therein.

The polymer film 7 is composed of the two layers of: a film body 8 as an acoustic matching layer; and an electrode pattern 9 which is formed on the side of the adhesive layer 6 in this film body 8, for example, made of a copper layer. Then, the end of this polymer film 7 protrudes from the layered portion in the piezoelectric element 1, and the tip of the protrusion is electrically connected to a grounded electric terminal (not shown). By the way, on the copper layer surface of the electrode pattern 9, a gold or nickel layer or the like is desired to be formed by depositing, plating or sputtering so that the oxidation is protected. On the surface of the film body 7, a second acoustic matching layer 11 made of a polymer material and the like for efficiently transmitting the ultrasonic waves is layered via an adhesive layer 10 that does not include the graphite powder (in order not to increase an acoustic impedance because it is located closely to the living body).

On the side of the positive electrode layer 3 in the piezoelectric element 1, an FPC 15 as a second film is layered via a thermosetting two-component type adhesive layer 14 in which the graphite powder is uniformly distributed therein. This FPC 15 is composed of a base unit 16 made of polyimide; and a conductive pattern 17 that is formed on the side of the piezoelectric element 1 on this base unit 16, correspondingly to the piezoelectric element 1, and for example, made of a copper layer. Also, both sides of the FPC 15 protrude from the layered portion in the piezoelectric element 1, and both ends of the protrusion are electrically connected to an electric terminal (not shown) for a signal. By the way, on the copper layer surface of the conductive pattern 17, the gold or nickel layer or the like is desired to be formed by depositing, plating or sputtering so that the oxidation is protected.

After the second acoustic matching layer 11, the adhesive layer 10, the polymer film 7, the adhesive layer 6, the first acoustic matching layer 5, the adhesive layer 4, the piezoelectric element 1, the adhesive layer 14, the FPC 15 and the like are layered, a high pressure is applied, and they are heated and pressure welled and firmly fixed.

Here, the high pressure (that is changed in accordance with the material and thickness of the piezoelectric element 1) indicates the pressure at which the piezoelectric element 1 is not broken (damaged) by the pressurization and also in the respective materials, the surfaces opposite to each other are sufficiently close to each other (as for the thickness of the adhesive layer between the surfaces, the surface is very close to 0, depending on the place).

Moreover, on the surface of the second acoustic matching layer 11, an acoustic lens 13 is layered via the adhesive layer 12. This is intended to converge the ultrasonic waves, and the upper side (the subject side) has the shape of a convex curve.

A backing material 18 is attached via an adhesive layer 19 to the side of the base unit 16 in the FPC 15 and mechanically supports the piezoelectric element 1 and acoustically damps the piezoelectric element 1 and consequently makes an ultrasonic pulse waveform short.

The operations of the ultrasonic probe having the foregoing configuration will be described below. A plurality of electrical signals, which are transmitted by a transmitter in the main body of the ultrasonic diagnostic apparatus (not shown), are applied via cables (not shown) and the FPC 15 to the plurality of piezoelectric elements 1 that are array-arranged. The piezoelectric element 1 excites (transmits) the ultrasonic waves (the mechanical vibration), correspondingly to the applied electrical signal. The excited ultrasonic waves are acoustically matched with the living body by the first acoustic matching layer 5, the second acoustic matching layer 11 and the acoustic lens 13, and converged by the acoustic lens 13 and then transmitted into the living body. Also, the piezoelectric element 1 generates (receives) an electrical signal, correspondingly to the ultrasonic waves returned from the living body, by the piezoelectric effect.

After the conversion into the electrical signal, it is transmitted via the cable to a receiver in the main body of the ultrasonic diagnostic apparatus. The signal received by the receiver is processed, and the picture of the received signal is displayed on a display in the main body of the ultrasonic diagnostic apparatus. Consequently, the picture of the body interior of a patient can be checked on a monitor. Those operation is similar to that of the conventional ultrasonic probe. However, the ultrasonic probe according to the present invention is not limited to the transmission/reception method of the main body as mentioned above.

By the way, between the ground electrode layer 2 in the piezoelectric element 1 and the conductive acoustic matching layer 5, between the conductive acoustic matching layer 5 and the polymer film 7 on which the conductive pattern 9 is formed, and between the positive electrode layer 3 in the piezoelectric element 1 and the conductive pattern 17 in the FPC 15, there are the thermosetting two-component type adhesive layers 4, 6 and 14, in which the graphite powder is uniformly distributed, respectively. The thermosetting two-component type adhesive layers 4, 6 and 14 in which the graphite powder is uniformly distributed will be described below.

As the graphite powder, is used one made into a ball-shaped particle. Also, a two-component type epoxy-based adhesive is used as the thermosetting two-component type adhesive. At first, a certain quantity of the graphite powder is mixed into a base material of the thermosetting two-component type adhesive. Here, as the ratio of the graphite powder is high, the conductivity is improved (the conduction resistance is decreased). However, the adhesive strength is decreased. Thus, it is necessary to determine the mixture ratio between the main component and the graphite powder, so as to exhibit the value under which the conductivity and the adhesive strength can be allowed, respectively, depending on the kinds and material qualities of the thermosetting two-component type adhesive, the graphite powder and the adherend. In the embodiment according to the present invention, the mixture ratio between the main component and the graphite powder is defined as 100:5, with respect to the weight ratio.

The main component of the thermosetting two-component type adhesive in which the graphite powder is mixed is agitated such that the graphite powder inside the main component is uniformly distributed. Also, in order to remove the air that is mixed into the main component by the agitation, a vacuum de-aeration is carried out.

Moreover, when the thermosetting two-component type adhesive in which the graphite powder is mixed is used, a curing agent is mixed into the main component of the thermosetting two-component type adhesive in which the graphite powder is mixed. Again, they are agitated, and the vacuum de-aeration is carried out. On the other hand, as mentioned above, the polymer film 7, the conductive acoustic matching layer 5, the piezoelectric element 1 and the FPC 15 are heated, cured and integrated in the situations in which the thermosetting two-component type adhesives where the graphite powder is uniformly distributed are used, respectively, and the high pressures are applied.

Thus, the thicknesses of the thermosetting two-component type adhesives in which those graphite powder is uniformly distributed are thin, and the respective conductive members are in the situation in which they are sufficiently close to each other. Thus, the tunnel effect, the Schottky conduction, the impurity conduction or the like causes the charges to be shifted. Also, the thicknesses of the adhesive layers are not constant. They exist at a certain probability, depending on the surface roughness of the opposite conductive member. Depending on the place, the thickness is very close to 0. In short, there are the positions at which the ground electrode layer 2 in the piezoelectric element 1 and the conductive acoustic matching layer 5, and also the positive electrode layer 3 in the piezoelectric element 1 and the conductive pattern 17 in the FPC 15, and further the conductive acoustic matching layer 5 and the conductive pattern 9 in the polymer film 7 are in contact, respectively. At those contact positions, the conduction resistances are small.

Also, with the surface roughness of the opposite conductive member, there is a geometric irregularity (convex and concave portions) on its surface. Thus, depending on the place, as mentioned above, there is the position at which the thickness is very close to 0, and reversely, there is the position at which the thickness is very thick. At the thick position, the effect of the tunnel effect, the Schottky conduction, the impurity conduction or the like is weak, which results in the increase in the conduction resistance. Here, since the thermosetting two-component type adhesive in which the graphite powder is uniformly distributed is used, the conductive graphite powder intruded into the convex and concave portions of the respective conductive members, and the conductors of the mutual materials are electrically connected. That is, the contact area between the conductor portions of the mutual materials is made larger, which reduces the irregularity in the conduction resistance of the electrical connector (refer to FIG. 3). As a result, the sensibility irregularity between the arrays can be reduced, and the generation of noise and the like can be prevented.

Here, the reason why the two-component type epoxy-based adhesive in which the graphite powder is mixed will be described below.

(1) Since the two-component type adhesive is selected, the curing temperature of the adhesive is decreased. For example, in a two-component type epoxy-based adhesive 353ND of US Epoxy Technology Company, its standard curing temperature and time are 60 deg C. and 90 minutes. Typically, for the conductive paste and the anisotropic conductive adhesive in which the curing temperatures are 100 deg C. or more, the piezoelectric element is not required to be exposed in a high temperature environment. Thus, the ultrasonic probe that can be easily manufactured can be provided without any deterioration in the performance of the piezoelectric element.

(2) Since the glass transition temperature is high such as 100 deg C. or more, this is superior in heat resistance. For example, the glass transition temperature of the two-component type epoxy-based adhesive 353ND of US Epoxy Technology Company is 124 deg C. Thus, this is superior in heat resistance and also confirms USP (the standard with regard to the safety tests of drugs and medicines for a medical service.

(3) Since the adhesive can be placed at a room temperature, this is superior in storage property. Typically, for the conductive paste and the anisotropic conductive adhesive that are required to be stored in a refrigerated state, the storage period of the two-component type epoxy-based adhesive 353ND of US Epoxy Technology Company is, for example, about one year in the room temperature storage.

(4) After the graphite powder is uniformly distributed in the main component of the adhesive, when the adhesive is used, the adhesive work can be immediately started by adding the curing agent. Thus, this is superior in working property.

(5) Both of the graphite powder and the two-component type epoxy-based adhesive 353ND are low in cost.

According to the ultrasonic probe in the first embodiment according to the present invention as mentioned above, when the first film in which the piezoelectric element, the conductive acoustic matching layer and the electrode pattern are formed and the second film in which the electrode pattern is formed are adhesively layered, the thermosetting two-component type adhesive in which the graphite powder is uniformly distributed is used, which can reduce the irregularity of the conduction resistance of the electrical connector. As a result, the sensibility irregularity between the arrays can be reduced. Also, the quality and the working property are excellent, and the cost is low.

By the way, the thermosetting two-component type adhesive is used as the first embodiment. However, instead of this, if a one-component type adhesive whose curing temperature is 100 deg C. or less can be used, it is naturally possible to further improve the working property.

The ultrasonic probe of the second embodiment according to the present invention will be described below.

In the ultrasonic probe in the second embodiment, a 10-point average roughness (Rz) on the surfaces of the electrode layers formed on both the surfaces of the piezoelectric element 1 in the ultrasonic probe in the first embodiment is set to a range from 3.5 μm to 6.5 μm. Moreover, an average particle diameter between the graphite powder of the thermosetting two-component type adhesive layers 4, 6 and 14 in which the graphite powder is uniformly distributed to adhere the polymer film 7, the conductive acoustic matching layer 5, the piezoelectric element 1 and the FPC 15, respectively, is set to a range from 3.5 μm to 6.5 μm.

Figure 2:
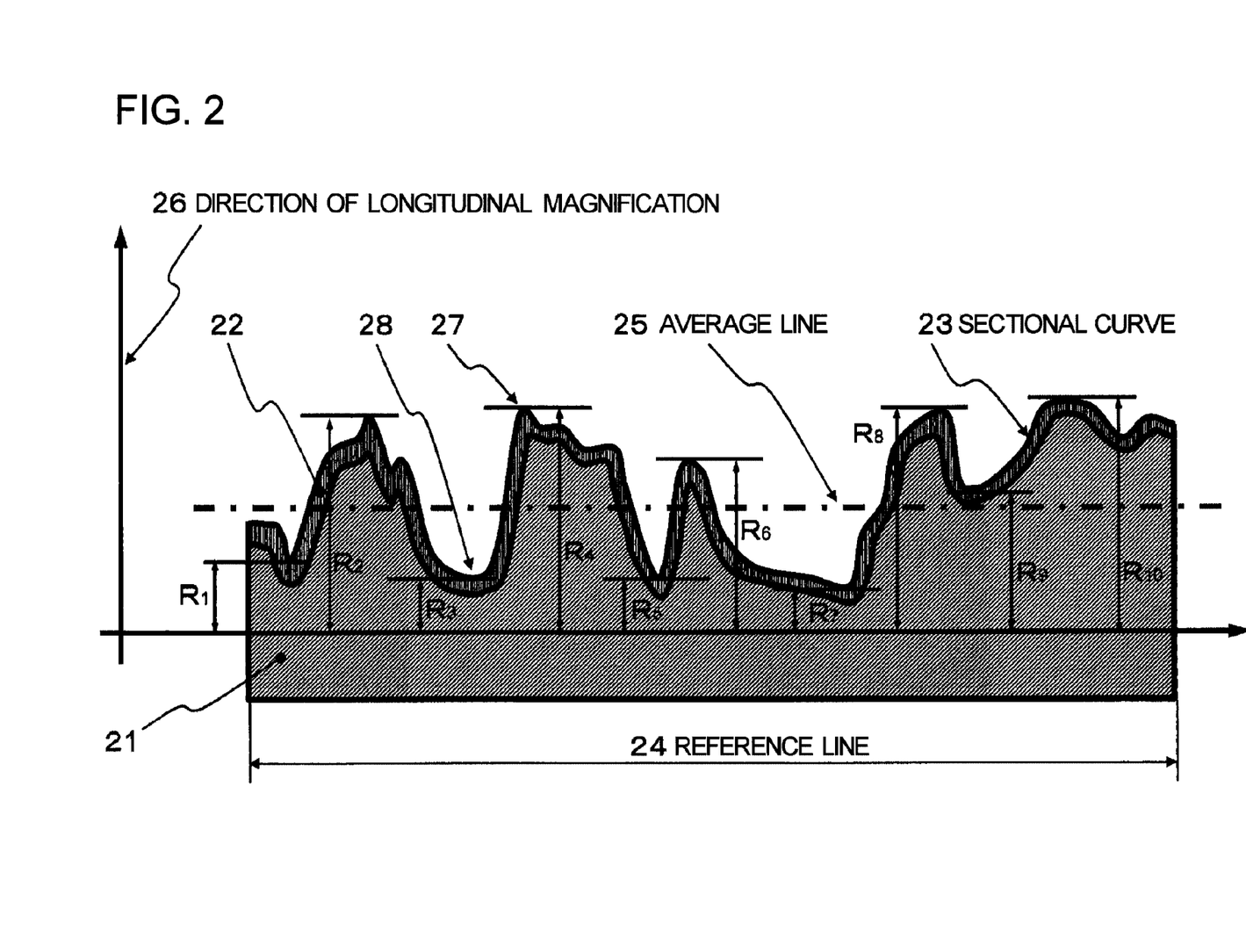
FIG. 2 is a view explaining a surface roughness of a piezoelectric element in a second embodiment according to the present invention.

FIG. 2 shows the shape (the roughness) of the surface on the section of a piezoelectric element 21.

A ground electrode layer 22 is a layer that is formed on the surface of the piezoelectric element 21 by the gold sputtering (the positive electrode layer 3 is similarly formed by the gold sputtering).

In the portion after only a standard length 24 is cut away from a sectional curve 23, the value (the 10-point average roughness) of a difference between: an average value of the heights of summits from the highest to the fifth that are measured in a longitudinal magnification direction 26 from a straight line which is parallel to an average line 25 and does not intersect the sectional curve; and an average value of the heights of valley floor from the deepest to the fifth is calculated from equation (1).

$$Rz=\{(R2+R4+R6+R8+R10)-(R1+R3+R5+R7+R9)\}/5 \quad (1)$$

Since the 10-point average roughness (Rz) on the surface of the electrode layers (the ground electrode layer 22 and the positive electrode layer 3) formed on both the surfaces of the piezoelectric element 21 is set to the range from 3.5 µm to 6.5 µm, the difference between the high and low portions, for example, in a mountain 27 and a valley floor 28 that are located on the sectional curve 23 is averagely located in the range from 3.5 µm to 6.5 µm. Thus, in the thermosetting two-component type adhesive in which the graphite powder is uniformly distributed, the average particle diameter of the graphite powder is set to the range from 3.5 µm to 6.5 µm. Hence, the particle of the graphite powder can easily intrude into the recess on the surface of the piezoelectric element 21.

Figure 3:
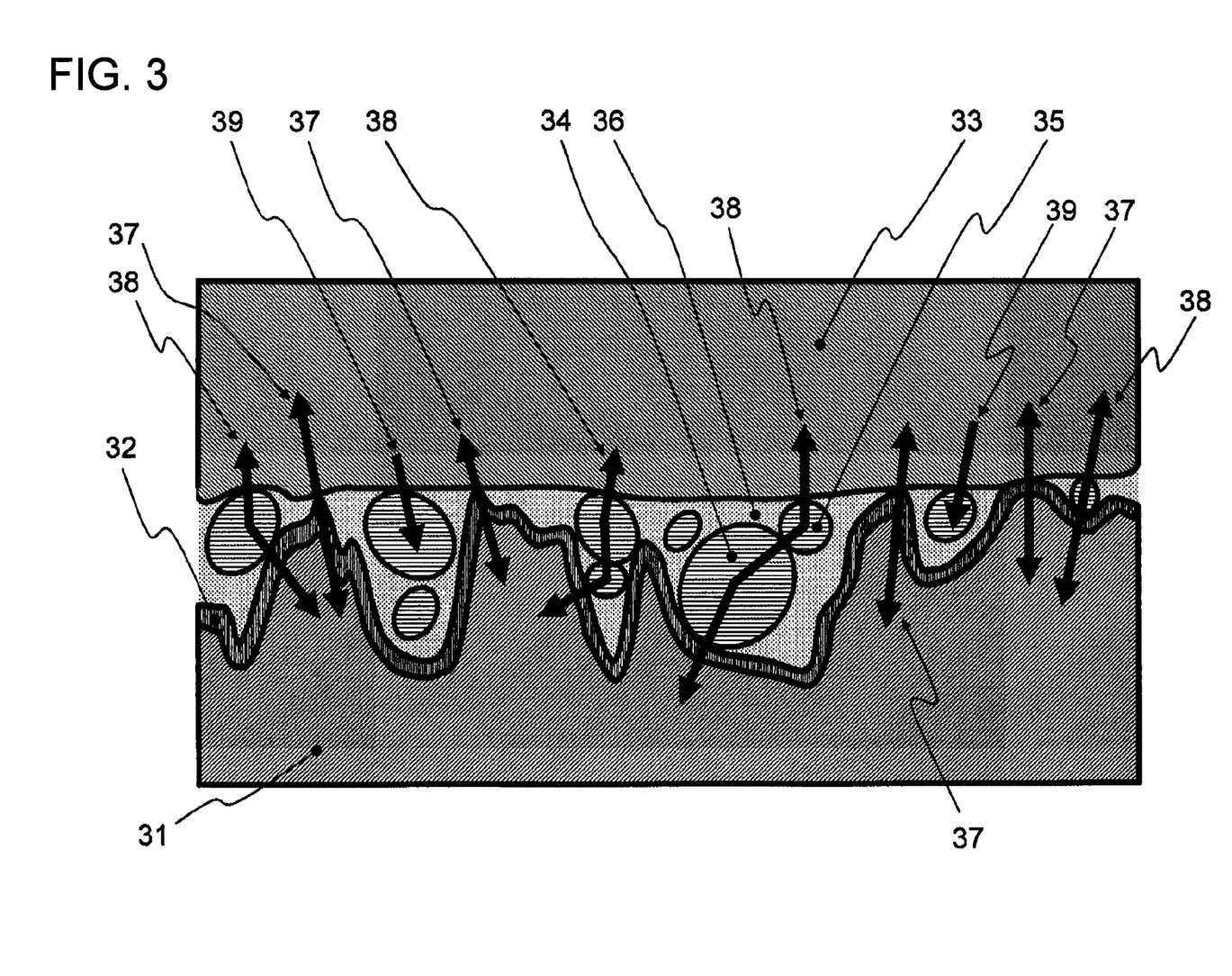
FIG. 3 is a sectional diagrammatic view of an adhesion boundary layer in the second embodiment according to the present invention.

FIG. 3 shows the sectional diagrammatic view of the adhesive boundary layer in the thermosetting two-component type adhesive in which the graphite powder is uniformly distributed, in the ultrasonic probe in the second embodiment according to the present invention. The other configurations do not differ from those of the first embodiment (FIG. 1).

A thermosetting two-component type adhesive 36 where graphite powder 34 having an average particle diameter in the range from 3.5 µm to 6.5 µm is uniformly distributed is coated on the surface of a ground electrode layer 32 formed on the surface of a piezoelectric element 31, and a conductive acoustic matching layer 33 is layered. When those materials are pressed and fixedly adhered to each other, in order to apply the high pressure, the graphite powder flied out from the recess on the surface of the piezoelectric element 31 is smashed, and its cut piece 35 intrudes into the other recess. The thermosetting two-component type adhesive 36 in which the graphite powder is uniformly distributed are heated. Consequently, they are fixedly adhered. Here, at a portion 37, the thickness of the adhesive is very close to 0. In short, this is the position at which the ground electrode layer 32 in the piezoelectric element 31 and the conductive acoustic matching layer 33 are in contact, and in this contact position, the conduction resistance is small. Also, as mentioned above, with the surface roughness of the opposite conductive material, there is the geographic irregularity (convex and concave) on the surface. Hence, depending on the place, as mentioned above, there is also the position at which the thickness of the adhesive is very close to 0, and reversely, there is the position at which the thickness is very thick.

As indicated at a portion 38, at the thick position, the graphite powder is filled. Thus, the conductors of the mutual materials are electrically connected. Even if the conductors of the mutual materials are not electrically connected, as shown at a portion 39, the graphite powder is filled in the recess. Thus, the respective conductive members are sufficiently close to each other. Hence, the tunnel effect, the Schottky conduction, the impurity conduction or the like causes the charges to be shifted.

As a result, the contact area between the conductors of the mutual materials is increased, thereby decreasing the irregularity of the conduction resistance of the electrical connector. Also, since the 10-point average roughness (Rz) on the surfaces of the electrode layers formed on both the surfaces of the piezoelectric element 31 is set to the range from 3.5 µm to 6.5 µm, the thermosetting two-component type adhesive 36 is immersed and cured in the gap on the surface of the piezoelectric element 31, the adhesive strength is increased by an anchor effect in which it carries out an action such as a pin or an wedge.

Also, in order to reserve the sensibility of the ultrasonic probe, in the piezoelectric element 31 and the conductive acoustic matching layer 33, the mutual materials are required to be very thinly adhered, thereby suppressing the absorption, reflection and dispersion losses of the ultrasonic waves, which are caused by the adhesive and the graphite powder inside the adhesive. Thus, the gap (the maximum adhesive layer thickness) between the mutual materials is desired to be 10 µm or less. On the other hand, as for the graphite powder that is made into the ball-shaped particle by the work for smashing to the shape of the ball, at present, in even in the smallest state, it can be set to the micro range from 3.5 µm to 6.5 µm with respect to the longitudinal axis of the ball-shaped particle.

As mentioned above, the 10-point average roughness (Rz) on the surfaces of the electrode layers formed on both the surfaces of the piezoelectric element 31 is required to be set to the range from 3.5 µm to 6.5 µm. Moreover, the average particle diameter (the length of the longitudinal axis) of the graphite powder in the thermosetting two-component type adhesive in which the graphite powder is uniformly distributed to adhere the piezoelectric element 31 and the conductive acoustic matching layer 33 is required to be set to the range from 3.5 µm to 6.5 µm.

By the way, the manufacturing method and the operating method of the second embodiment are similar to those of the first embodiment. Thus, their explanations are omitted.

As mentioned above, according to the ultrasonic probe in the second embodiment according to the present invention, the 10-point average roughness (Rz) on the surfaces of the electrode layers formed on both the surfaces of the piezoelectric element is set to the range from 3.5 µm to 6.5 µm, and the average particle diameter of the graphite powder in the thermosetting two-component type adhesive in which the graphite powder is uniformly distributed is set to the range from 3.5 µm to 6.5 µm. Thus, the graphite powder intrudes into the concave and convex portions on the piezoelectric element surface, and the adhesive property between the mutual materials, namely, the contact area between the mutual materials is increased, thereby decreasing the irregularity of the conduction resistance of the electric connector. This results in the reduction in the sensibility irregularity between the arrays. Also, the concave depth of the piezoelectric element and the diameter of the graphite powder are equal in size. Thus, since the mutual materials can be very thinly adhered, the absorption, reflection and dispersion losses of the ultrasonic waves that are caused by the adhesive and the graphite powder inside the adhesive can be suppressed, which results in the improvement of the sensibility of the ultrasonic probe.

Figure 4:
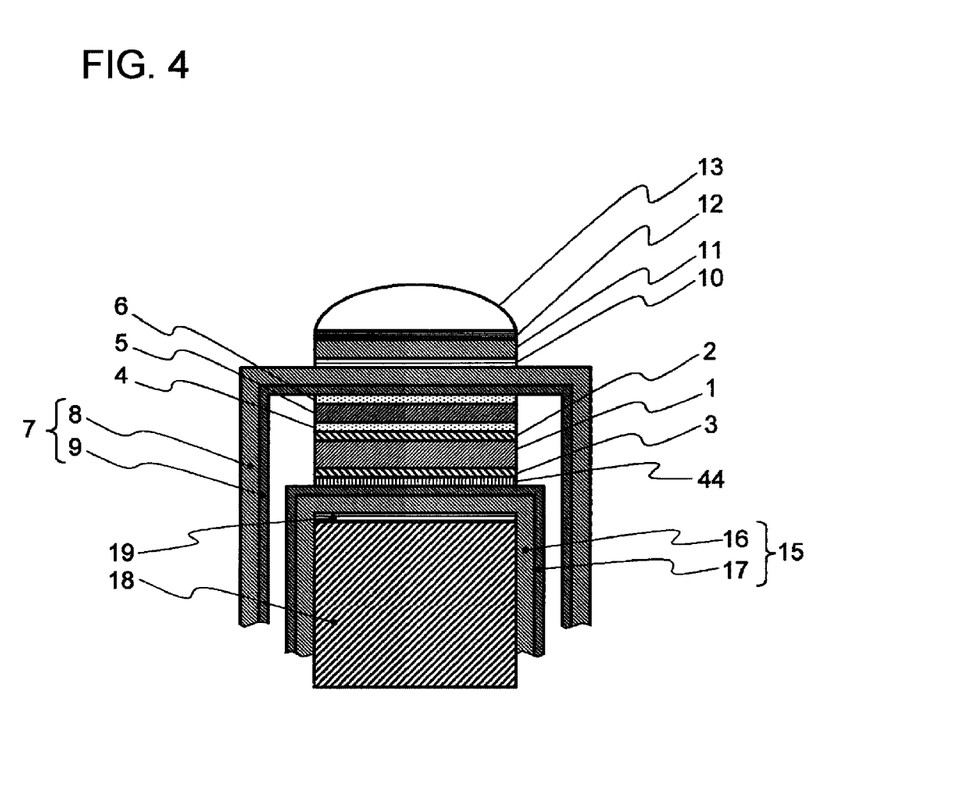
FIG. 4 is a schematic sectional view of an ultrasonic probe in a third embodiment according to the present invention.

Next, FIG. 4 shows the ultrasonic probe in the third embodiment according to the present invention. The difference between the third embodiment according to the present invention and the first embodiment lies in a configuration in which the FPC 15 is layered on the side of the positive electrode layer 3 in the piezoelectric element 1, via a thermosetting two-component type adhesive layer 44 where tungsten powder is uniformly distributed therein. On the side of the ground electrode layer 2 in the piezoelectric element 1, the conductive acoustic matching layer 5 for efficiently transmitting the ultrasonic waves is layered via a thermosetting two-component type adhesive layer 4 in which the graphite powder is uniformly distributed therein. Moreover, on the acoustic matching layer 5, the polymer film 7 as the first film is layered via a thermosetting two-component type adhesive layer 6 in which the graphite powder is uniformly distributed therein. For example, graphite and the like are used for the conductive acoustic matching layer 5.

Thus, as compared with the conventional ultrasonic probe that uses the thermosetting two-component type adhesive to which the graphite powder is not added, the differences of the acoustic impedances between the adhesive layer 4 and the conductive acoustic matching layer 5 and between the conductive acoustic matching layer 5 and the adhesive layer 6 are reduced, thereby suppressing the reflection loss of the ultrasonic waves that are generated on the boundary surface between acoustic media. On the other hand, on the side of the positive electrode layer 3 in the piezoelectric element 1, the FPC 15 is layered via the thermosetting two-component type adhesive layer 44 in which the tungsten powder is uniformly distributed therein. This FPC 15 is composed of: the base unit 16 made of polyimide; and the conductive pattern 17 that is formed on the side of the piezoelectric element 1 on this base unit 16, correspondingly to the piezoelectric element 1, and for example, made of a copper layer. Also, on the side of the base unit 16 in the FPC 15, a backing material 18 is attached via an adhesive layer 19.

The ultrasonic waves transmitted from the piezoelectric element 1 are also transmitted to the backing material 18. Since the ultrasonic waves transmitted to the backing material 18 are unnecessary, they must be attenuated inside the backing material 18 so as not to be again returned to the piezoelectric element 1. To do so, the unnecessary ultrasonic waves emitted to the rear of the piezoelectric element 1 must be efficiently transmitted to the backing material 18. On the side of the positive electrode layer 3 in the piezoelectric element 1, the FPC 15 is layered via the thermosetting two-component type adhesive layer 44 in which the tungsten powder is uniformly distributed therein. Thus, the difference of the acoustic impedance between the adhesive layer 44, and the conductive pattern 17 made of the copper layer located on the FPC 15, and the backing material 18 is reduced, thereby suppressing the reflection loss of the ultrasonic waves that are generated on the boundary surface between the acoustic media. As a result, the unnecessary ultrasonic waves emitted to the rear of the piezoelectric element 1 are not again returned to the piezoelectric element 1.

As mentioned above, according to the ultrasonic probe in the third embodiment according to the present invention, the graphite powder is uniformly distributed in: the adhesive layer 1 that is located between the first electrode layer formed on one side of the piezoelectric element and one or more conductive acoustic matching layers; and the adhesive layer 2 that is located between one or more conductive acoustic matching layers and the first film on which the electrode pattern is formed, and the tungsten powder is uniformly distributed in the adhesive layer 3 that is located between the second electrode layer formed on the other side of the piezoelectric element and the second film on which the electrode pattern is formed. Thus, the reflection loss of the ultrasonic waves generated on the boundary surface between the acoustic media is reduced, which results in the improvement of the sensibility of the ultrasonic probe.

The ultrasonic probe in the fourth embodiment according to the present invention will be described below. In recent years, a fact that the sensibility can be made high and the frequency band can be made wide, because the piezoelectric element is made of the complex piezoelectric body in which the pole of the piezoelectric element is embedded in a resin sheet.

Figure 5A:
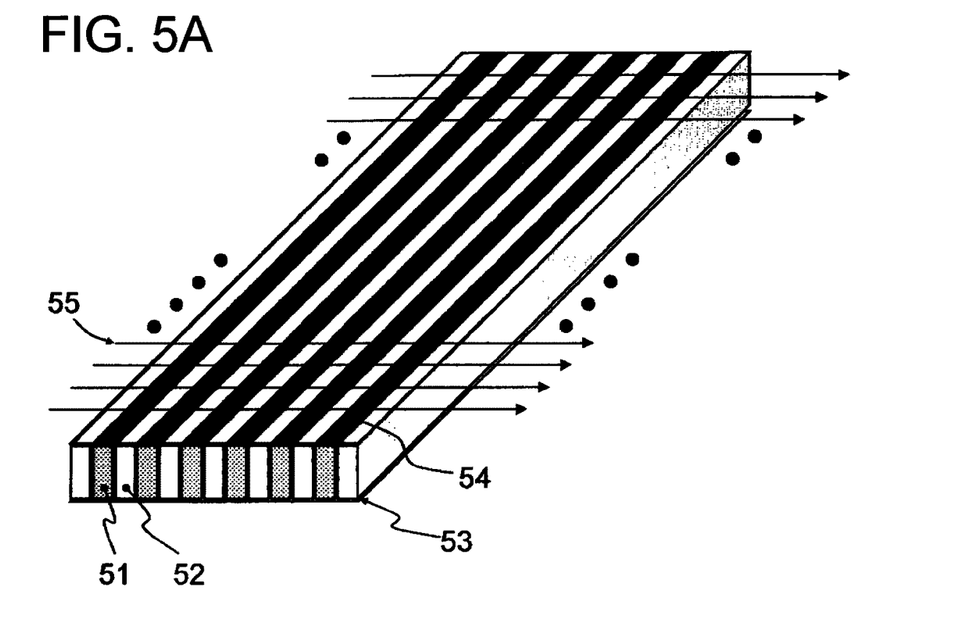
FIG. 5A is a perspective view of a complex piezoelectric body in a fourth embodiment according to the present invention.
Figure 5B:
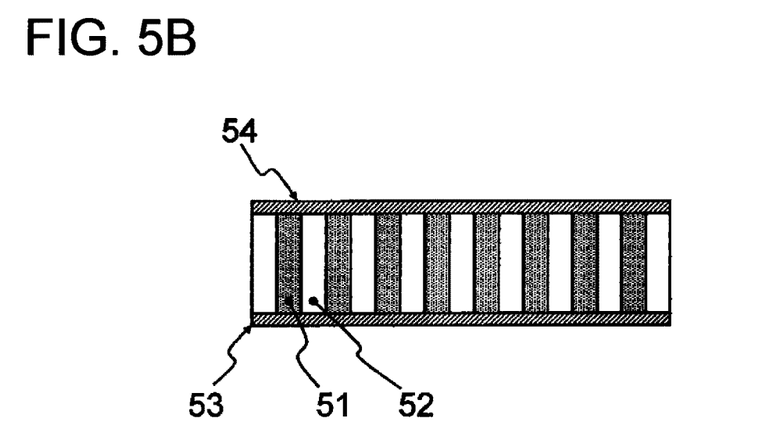
FIG. 5B is a side sectional view of the complex piezoelectric body in the fourth embodiment according to the present invention.

Conventionally, as the method of manufacturing the complex piezoelectric body, a dicing and filling method is used in which a piezoelectric element plate is cut into an angular shape by a dicing-cut, and resin is embedded therein. FIGS. 5A and 5B are the perspective view and the side view that show the complex piezoelectric body, respectively. A piezoelectric element pole column 51 is such that the piezoelectric element plate is cut into the angular shape by the dicing-cut, and an epoxy resin 52 is vacuum-immersed into the gap of the piezoelectric element pole column 51, and the top and bottom surfaces are removed by polishing, and after it is made into a predetermined thickness, sputter-film-formation of chrome and gold is performed, and electrodes 53, 54 are formed. The complex piezoelectric body manufactured as mentioned above is assembled into the ultrasonic probe and diced at a predetermined pitch. Consequently, the complex piezoelectric body is divided into a plurality of arrays 55 that are electrically independent of each other.

In the conventional manufacturing method, the foregoing polishing work requires that the surface on which the piezoelectric element made of the epoxy resin, the ceramic and the like, and the different material are alternately arranged is flatly polished. However, it was difficult to flatten the boundary between the different materials whose hardnesses are different.

Also, the foregoing sputter-film-formation step has a problem that the difference of a thermal expansion coefficient causes a crack to be generated on the boundary between the different materials. Thus, the complex piezoelectric body has a problem that the difficulty in its manufacturing process (its quality reservation) causes its cost to be expensive.

Figure 6:
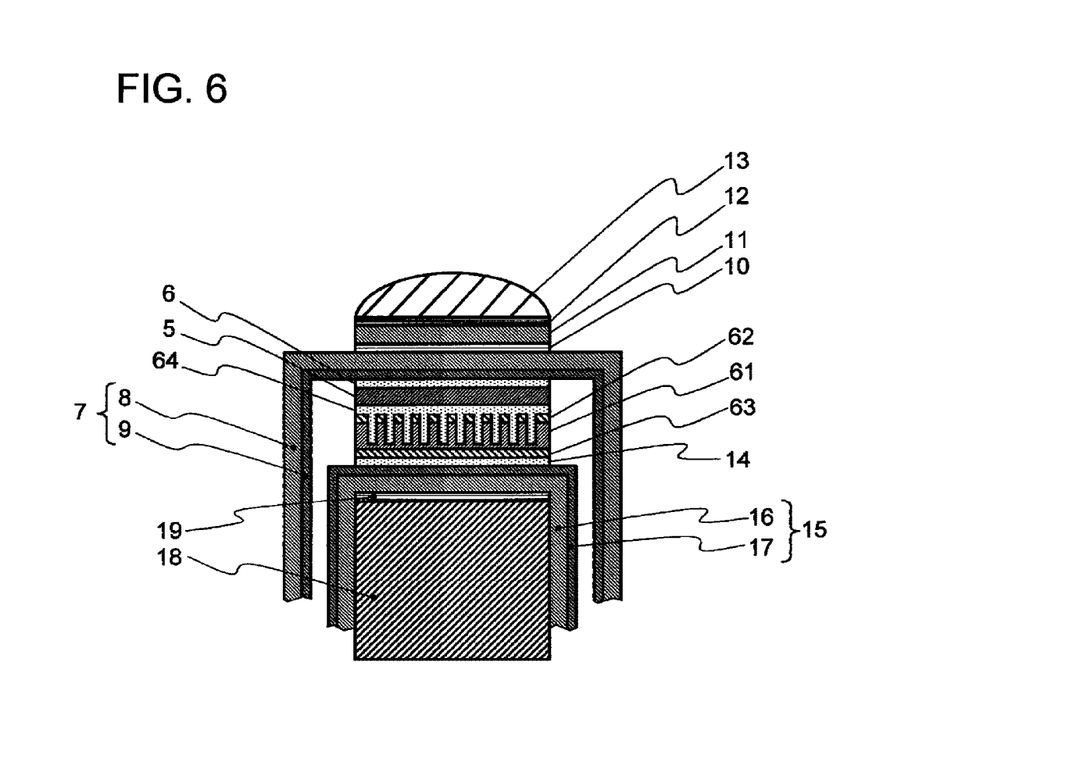
FIG. 6 is a schematic sectional view of an ultrasonic probe in the fourth embodiment according to the present invention.

FIG. 6 shows the ultrasonic probe in the fourth embodiment according to the present invention. In the ultrasonic probe in the fourth embodiment according to the present invention, the piezoelectric element plate on which the sputter-film-formation of chrome and gold is already performed is used, and the pole column work of the piezoelectric element plate is carried out in the manufacturing process for the ultrasonic probe, and the epoxy resin is immersed into the gap of the piezoelectric element pole column. Consequently, the complex piezoelectric body is assembled into the ultrasonic probe. As a result, the polishing work and the electrode forming work through the sputter-film-formation, which are conventionally required after the epoxy resin is vacuum-immersed into the gap of the piezoelectric element pole column, can be omitted, which makes the quality high.

The difference between the fourth embodiment according to the present invention and the first embodiment lies in a configuration that the piezoelectric element for generating the ultrasonic waves uses a complex piezoelectric body 56 where the piezoelectric element in which the electrodes are formed on both surfaces is cut into the angular shape, and resin is embedded. Thus, the configurations and the functions are omitted here. The manufacturing method of the ultrasonic probe in the fourth embodiment according to the present invention is substantially equal to the manufacturing method of the ultrasonic probe in the first embodiment, with regard to the basic flow. However, the difference lies in the following mechanism. That is, because of the relation of the timing of the dicing, after on both sides of a piezoelectric element 61 that contains a ground electrode layer 62 and a positive electrode layer 63 which are formed on both the surfaces by the gold sputtering, the polymer film 7, the FPC 15 and the like are layered via the thermosetting two-component type adhesive layer 14 in which the graphite powder is uniformly distributed, the high pressure is not applied, in short, after both the sides are layered on the piezoelectric element, the high pressure is not applied, and then, the high pressure is applied from the layered portion for each one side, and the heating is carried out, and the dicing is carried out as described below.

With regard to the dicing, from the side of the polymer film 7 and from the front of the piezoelectric element 61 to the longitudinal axis direction, the dicing is carried out at a predetermined pitch, and the piezoelectric element pole column is manufactured.

Here, the cutting is not executed up to the positive electrode layer 63 in the piezoelectric element 61, or up to the conductive pattern 17 in the FPC 15. That is, the positive electrode layer 63 in the piezoelectric element 61, or the conductive pattern 17 in the FPC 15 is not divided.

A thermosetting two-component type adhesive 64 in which the graphite powder is uniformly distributed in the gap of the piezoelectric element pole column 61 is sent into a notch groove. Moreover, the conductive acoustic matching layer 5 is layered on the ground electrode layer 62 on the piezoelectric element 61. The thermosetting two-component type adhesive layer 6 in which the graphite powder is uniformly distributed is used to layer the polymer film 7 on the conductive acoustic matching layer 5. By the way, the electrode pattern 9 formed on the polymer film 7 is made opposite to the side of the conductive acoustic matching layer 5.

On the polymer film 7, the second acoustic matching layer 11 is layered by using the adhesive layer 10. The high pressure is applied, and they are heated. Consequently, they are pressed and fixedly adhered. From the side of the FPC 15, the dicing is executed at a predetermined pitch, and the piezoelectric element 61 is divided into a plurality of arrays that are electrically independent of each other. Next, both the sides of the FPC 15 and both the sides of the polymer film 7 are bent and made into the shape shown in FIG. 6. The acoustic lens 13 is attached by using the silicon-based adhesive layer 12.

In the foregoing manufacturing process, the formation of the complex piezoelectric body 56 results in the drastic reduction in the size of the division electrode of the ground electrode layer 62. Thus, in the conventional adhering method, the irregularity of the conduction resistance of the electric connector is further increased. Depending on the condition, there is a case that the electrode in which the conduction cannot be reserved is formed. However, according to the ultrasonic probe in the fourth embodiment according to the present invention, the thermosetting two-component type adhesive layers 6, 64 and 14 in which the graphite powder is uniformly distributed to adhere the polymer film 7, the conductive acoustic matching layer 5, the piezoelectric element 61 and the FPC 15 are used. Thus, even if the size of the division electrode of the ground electrode layer 62 becomes very small when the complex piezoelectric body 56 is formed, the conductions of the respective electric connectors can be reserved, and the irregularities of the conduction resistances of the electric connectors can be suppressed to small values. As a result, the sensibility irregularity between the arrays becomes small.

Figure 7A:
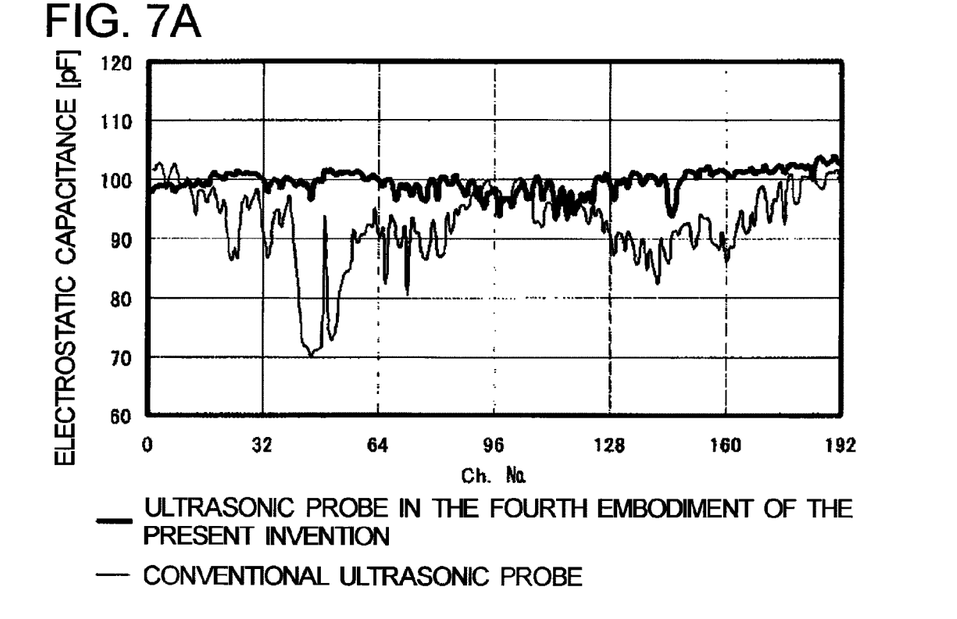
FIG. 7A is a view showing an electrostatic capacitance of the ultrasonic probe in the fourth embodiment according to the present invention.
Figure 7B:
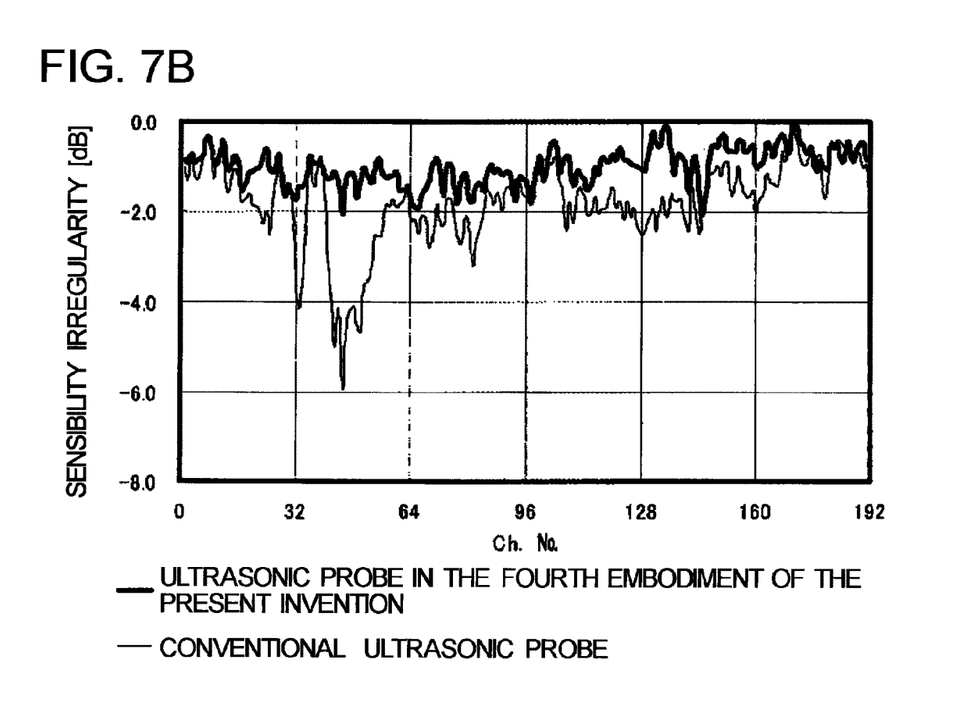
FIG. 7B is a view showing a sensitivity irregularity of the ultrasonic probe in the fourth embodiment according to the present invention.

FIGS. 7A and 7B show their effects. FIG. 7A shows the irregularities of the electrostatic capacitances between the respective channels, in the ultrasonic probe in the fourth embodiment according to the present invention to which the complex piezoelectric body manufactured by the foregoing manufacturing process is applied and the ultrasonic probe to which the complex piezoelectric body manufactured by the foregoing manufacturing process is applied and in which the thermosetting two-component type adhesive without any graphite powder is used. FIG. 7B similarly shows the sensibility irregularity between the respective channels. When the graphite powder is not included in the adhesive for adhering the polymer film 7, the conductive acoustic matching layer 5, the piezoelectric element 61 and the FPC 15, the conduction reservation of the electric connector between the respective channels is not perfect, and the irregularity of the conduction resistance is great, thereby increasing the electrostatic capacitance and the sensibility irregularity. In the ultrasonic probe in the fourth embodiment according to the present invention, it is evident that the electrostatic capacitance and the sensibility irregularity are small.

As mentioned above, according to the ultrasonic probe in the fourth embodiment according to the present invention, in the manufacturing process for the ultrasonic probe, the pole column work of the piezoelectric element pole column is carried out, and the epoxy resin is immersed into the gap of the piezoelectric element pole column. The polymer film, the conductive acoustic matching layer, the complex piezoelectric element, and the electric connector of the FPC are pressed and fixedly adhered by the thermosetting two-component type adhesive in which the graphite powder is uniformly distributed. As a result, the ultrasonic probe to which the complex piezoelectric body 56 is applied can be manufactured at the low cost. Also, with the complex piezoelectric body 56, the acoustic impedance of the piezoelectric element is decreased, and the matching property with the living body organization is made better. Thus, the acoustic transmission loss is reduced, and the sensibility of the ultrasonic probe is improved.

By the way, the foregoing explanations are carried out by using the ultrasonic probe of a linear type. However, this can be similarly embodied even in the other ultrasonic probes of a convex type and a matrix array type.

INDUSTRIAL APPLICABILITY

As mentioned above, in the ultrasonic probe according to the present invention, when the first film in which the piezoelectric element, the conductive acoustic matching layer and the electrode pattern are formed and the second film in which the electrode pattern is formed are layered and adhered, the thermosetting two-component type adhesive in which the graphite powder is uniformly distributed is used, thereby reducing the irregularity of the conduction resistance of the electric connector. As a result, this has the effect that the sensibility irregularity between the arrays is reduced, and this is effective as the ultrasonic probe that is connected to the ultrasonic diagnostic apparatus, in which the ultrasonic waves are emitted to the body interior of the examinee, and the picture of the body interior can be displayed from the ultrasonic waves reflected by the boundary between the respective body interior elements.

The invention claimed is:

1. An ultrasonic probe comprising:
   a piezoelectric element;
   a first electrode layer formed on one side of said piezoelectric element;
   at least one conductive acoustic matching layer layered via an adhesive layer on said first electrode layer;
   a first film layered via an adhesive layer on said at least one conductive acoustic matching layer, an electrode pattern being formed on an adhesive layer side of said first film;
   a second electrode layer formed on the other side of said piezoelectric element; and
   a second film layered via an adhesive layer on said second electrode layer, an electrode pattern being formed on an adhesive layer side of said second film;
   wherein:
   graphite powder is uniformly distributed in at least one of said adhesive layers, a thickness of the adhesive layer on the first electrode layer is non-constant, such that in at least one position, the first electrode layer and the conductive acoustic matching layer are in contact and in another position, the first electrode layer and the conductive acoustic matching layer are spaced a distance apart from each other, in the position in which the first electrode layer and the conductive acoustic matching layer are spaced apart, a recess is formed between the first electrode layer and the conductive acoustic matching layer, and the graphite powder is disposed in the recess between the first electrode layer and the conductive acoustic matching layer, such that the first electrode layer is electrically connected to the conductive acoustic matching layer through the graphite powder.

2. The ultrasonic probe according to claim 1, wherein a backing material is provided on the other side of said second film, and each of said adhesive layers comprises a thermosetting two-component type adhesive.

3. The ultrasonic probe according to claim 1, wherein a 10-point average roughness (Rz) on the surfaces of the electrode layers formed on both surfaces of said piezoelectric element is in a range from 3.5 µm to 6.5 µm, and wherein an average particle diameter of said graphite powder is in a range from 3.5 µm to 6.5 µm.

4. The ultrasonic probe according to claim 1, wherein the graphite powder is uniformly distributed in (i) the adhesive layer which is located between the first electrode layer formed on the one side of said piezoelectric element and the at least one conductive acoustic matching layer, and (ii) the adhesive layer which is located between the at least one conductive acoustic matching layer and the first film on which the electrode pattern is formed, and wherein tungsten powder is uniformly distributed in the adhesive layer which is located between the second electrode layer formed on the other side of said piezoelectric element and the second film on which the electrode pattern is formed.

5. The ultrasonic probe according to claim 1, wherein said piezoelectric element comprises a complex piezoelectric body in which said piezoelectric element where electrodes are formed on both surfaces is cut into an angular shape, and resin is embedded.

6. The ultrasonic probe according to claim 1, wherein an electrical connection is formed between the at least one conductive acoustic matching layer and the piezoelectric element through the graphite powder in the adhesive layer on said first electrode layer.

* * * * *